United States Patent
Chojin et al.

(10) Patent No.: US 8,647,343 B2
(45) Date of Patent: Feb. 11, 2014

(54) SURGICAL FORCEPS FOR SEALING AND DIVIDING TISSUE

(75) Inventors: Edward M. Chojin, Boulder, CO (US); David M. Garrison, Longmont, CO (US); Jennifer S. Harper, Westminster, CO (US); Glenn A. Horner, Boulder, CO (US); Duane E. Kerr, Loveland, CO (US); Jessica E. C. Olson, Frederick, CO (US); Kathy E. Rooks, Aurora, CO (US); Geneva Ladtkow, Arvada, CO (US)

(73) Assignee: Covidien LP, Mansfield, MA (US)

( * ) Notice: Subject to any disclaimer, the term of this patent is extended or adjusted under 35 U.S.C. 154(b) by 810 days.

(21) Appl. No.: 12/821,253

(22) Filed: Jun. 23, 2010

(65) Prior Publication Data

US 2011/0319886 A1    Dec. 29, 2011

(51) Int. Cl.
*A61B 18/14*       (2006.01)

(52) U.S. Cl.
USPC ............................................ 606/51; 606/207

(58) Field of Classification Search
USPC ................................. 606/46, 51, 52, 205–207
See application file for complete search history.

(56) References Cited

U.S. PATENT DOCUMENTS

| | | |
|---|---|---|
| D263,020 S | 2/1982 | Rau, III |
| D295,893 S | 5/1988 | Sharkany et al. |
| D295,894 S | 5/1988 | Sharkany et al. |
| 5,190,541 A * | 3/1993 | Abele et al. ..................... 606/46 |
| D348,930 S | 7/1994 | Olson |
| 5,613,499 A | 3/1997 | Palmer et al. |
| D384,413 S | 9/1997 | Zlock et al. |
| 5,700,261 A | 12/1997 | Brinkerhoff |
| D424,694 S | 5/2000 | Tetzlaff et al. |
| D425,201 S | 5/2000 | Tetzlaff et al. |
| D449,886 S | 10/2001 | Tetzlaff et al. |
| 6,361,534 B1 | 3/2002 | Chen et al. |
| D457,958 S | 5/2002 | Dycus et al. |
| D457,959 S | 5/2002 | Tetzlaff et al. |
| 6,425,896 B1 * | 7/2002 | Baltschun et al. .............. 606/51 |
| D493,888 S | 8/2004 | Reschke |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

*Primary Examiner* — Michael Peffley

(57) ABSTRACT

A forceps includes an end effector assembly including a pair of jaw members disposed in opposing relation relative to one another. At least one jaw member is moveable relative to the other between a spaced apart position, a first approximated position, and a second approximated position. The jaw members are configured to apply a pre-determined pressure to tissue disposed therebetween in each of the first and second approximated positions. A sealing pressure is applied to tissue disposed between the jaw members when the jaw members are in the first approximated position. A cutting pressure is applied to tissue disposed between the jaw members when the jaw members are in the second approximated position.

4 Claims, 5 Drawing Sheets

(56) References Cited

U.S. PATENT DOCUMENTS

| | | | |
|---|---|---|---|
| D496,997 S | 10/2004 | Dycus et al. | |
| D499,181 S | 11/2004 | Dycus et al. | |
| D509,297 S | 9/2005 | Wells | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| 7,270,660 B2 | 9/2007 | Ryan | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| 7,621,910 B2 | 11/2009 | Sugi | |
| 7,686,804 B2 | 3/2010 | Johnson et al. | |
| 7,717,914 B2 | 5/2010 | Kimura | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 8,035,129 B2 | 10/2011 | Ramaswamy et al. | |
| 8,112,871 B2 | 2/2012 | Brandt et al. | |
| 8,133,254 B2 | 3/2012 | Dumbauld et al. | |
| 8,162,965 B2 | 4/2012 | Reschke et al. | |
| 8,187,273 B2 | 5/2012 | Kerr et al. | |
| 8,226,650 B2 | 7/2012 | Kerr | |
| 8,251,994 B2 | 8/2012 | Mckenna et al. | |
| 8,266,783 B2 | 9/2012 | Brandt et al. | |
| 8,277,446 B2 | 10/2012 | Heard | |
| 8,287,536 B2 | 10/2012 | Mueller et al. | |
| 8,292,067 B2 | 10/2012 | Chowaniec et al. | |
| 8,292,886 B2 | 10/2012 | Kerr et al. | |
| 8,323,310 B2 * | 12/2012 | Kingsley | 606/207 |
| 8,343,150 B2 | 1/2013 | Artale | |
| 8,343,151 B2 | 1/2013 | Siebrecht et al. | |
| 8,357,159 B2 | 1/2013 | Romero | |
| 8,388,647 B2 | 3/2013 | Nau, Jr. et al. | |
| 8,409,247 B2 | 4/2013 | Garrison et al. | |
| 8,430,876 B2 | 4/2013 | Kappus et al. | |
| 8,439,911 B2 | 5/2013 | Mueller | |
| 8,469,991 B2 | 6/2013 | Kerr | |
| 8,469,992 B2 | 6/2013 | Roy et al. | |
| 2003/0018332 A1 | 1/2003 | Schmaltz et al. | |
| 2003/0171747 A1 | 9/2003 | Kanehira et al. | |
| 2008/0004616 A1 | 1/2008 | Patrick | |
| 2008/0015567 A1 * | 1/2008 | Kimura | 606/41 |
| 2008/0045947 A1 | 2/2008 | Johnson et al. | |
| 2009/0187188 A1 | 7/2009 | Guerra et al. | |
| 2010/0204697 A1 | 8/2010 | Dumbauld et al. | |
| 2010/0204698 A1 | 8/2010 | Chapman et al. | |
| 2010/0217258 A1 | 8/2010 | Floume et al. | |
| 2010/0249769 A1 | 9/2010 | Nau, Jr. et al. | |
| 2010/0280511 A1 | 11/2010 | Rachlin et al. | |
| 2011/0034918 A1 | 2/2011 | Reschke | |
| 2011/0046623 A1 | 2/2011 | Reschke | |
| 2011/0054468 A1 | 3/2011 | Dycus | |
| 2011/0054471 A1 | 3/2011 | Gerhardt et al. | |
| 2011/0060334 A1 | 3/2011 | Brandt et al. | |
| 2011/0060335 A1 | 3/2011 | Harper et al. | |
| 2011/0071523 A1 | 3/2011 | Dickhans | |
| 2011/0073594 A1 | 3/2011 | Bonn | |
| 2011/0077648 A1 | 3/2011 | Lee et al. | |
| 2011/0082494 A1 | 4/2011 | Kerr et al. | |
| 2011/0118736 A1 | 5/2011 | Harper et al. | |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026179 | 12/2005 |
| DE | 20 2007 009317 | 10/2007 |
| DE | 19738457 | 1/2009 |
| EP | 1159926 | 12/2001 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan., 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

(56) References Cited

OTHER PUBLICATIONS

Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, July 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol.234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.

(56) References Cited

OTHER PUBLICATIONS

Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.

* cited by examiner

SURGICAL FORCEPS FOR SEALING AND DIVIDING TISSUE

BACKGROUND

The present disclosure relates to surgical instruments. More particularly, the present disclosure relates to surgical forceps for sealing and/or cutting tissue.

TECHNICAL FIELD

Electrosurgical forceps utilize both mechanical clamping action and electrical energy to effect hemostasis by heating tissue and blood vessels to coagulate, cauterize and/or seal tissue. As an alternative to open forceps for use with open surgical procedures, many modern surgeons use endoscopic or laparoscopic instruments for remotely accessing organs through smaller, puncture-like incisions or natural orifices. As a direct result thereof, patients tend to benefit from less scarring and reduced healing time.

Endoscopic instruments, for example, are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue. Typically, after a vessel or tissue is sealed, the surgeon advances a knife to sever the sealed tissue disposed between the opposing jaw members.

SUMMARY

The present disclosure relates to a surgical forceps including an end effector assembly. The end effector assembly includes a pair of jaw members disposed in opposing relation relative to one another. One or both jaw members are moveable relative to the other between a spaced-apart position, a first approximated position and a second approximated position. The jaw members are configured to apply a pre-determined pressure to tissue disposed between the jaw members in the first and second approximated positions. More specifically, a sealing pressure is applied to tissue disposed between the jaw members when the jaw members are in the first approximated position. When the jaw members are in the second approximated position, a cutting pressure is applied to tissue disposed therebetween.

In one embodiment, one or both of the jaw members are adapted to connect to an electrosurgical energy source to communicate energy to tissue disposed between the jaw members to seal tissue disposed therebetween when the jaw members are in the first approximated position.

In another embodiment, a knife assembly and a knife channel defined within one or both of the jaw members are provided. The knife assembly includes a knife blade that, upon activation, is configured to translate distally to extend into the knife channel(s) to cut tissue disposed between the jaw members.

In still another embodiment, an opposing surface of each jaw member defines a complementary stepped portion. When the jaw members are moved to the second approximated position, tissue disposed between the jaw members is cut by the engagement of the complementary stepped portions. The complementary stepped portions may be defined longitudinally along the jaw members such that a distal end of each jaw member is offset from a proximal end of each jaw member or, alternatively, the complementary stepped portions may be defined laterally across the jaw members such that a first side of each jaw member is offset from a second side of each jaw member.

In yet another embodiment, one of the jaw members includes a protrusion, or flange extending longitudinally along an opposed surface thereof and the other jaw member includes a complementary recess similarly extending longitudinally along an opposed surface thereof. When the jaw members are moved to the second approximated position, the flange engages the recess to cut tissue disposed between the jaw members.

In still yet another embodiment, one of the jaw members includes a plurality of protrusions disposed along an opposed surface thereof and the other jaw member includes a plurality of complementary recesses extending longitudinally along an opposed surface thereof. Each recess is configured to engage one of the protrusions to cut tissue disposed therebetween when the jaw members are moved to the second approximated position.

In another embodiment, one or both of the jaw members includes a ceramic bar disposed thereon and extending longitudinally therealong. The ceramic bar is configured to cut tissue disposed between the jaw members upon movement of the jaw members to the second approximated position.

In still yet another embodiment, a fixed blade positioned within one of the jaw members. The jaw member also includes an opposed surface moveably coupled thereto. More specifically, the opposed surface is moveable with respect to the jaw member between a spaced position and a closer position. Upon movement of the jaw members to the second approximated position, the opposed surface is moved to the closer position with respect to the jaw member such that the fixed blade is urged through tissue disposed between the jaw members to cut tissue disposed therebetween. The opposed surface may be coupled to the jaw member by a spring mechanism. Further, the spring mechanism may be configured to bias the opposed surface toward the spaced position.

A method of sealing and dividing tissue is also provided in accordance with the present disclosure. The method includes providing a forceps according to any of the embodiments discussed above. The jaw members are moved to the spaced apart position and the forceps is positioned such that tissue is disposed between the jaw members. The jaw members are then moved from the spaced-apart position to the first approximated position where the sealing pressure is applied to seal tissue disposed between the jaw members. Next, the jaw members are moved to the second approximated position where the cutting pressure is applied to cut tissue disposed between the jaw members.

In one embodiment, in order to seal tissue disposed between the jaw members, electrosurgical energy is applied to the jaw member(s) when the jaw members are in the first approximated position.

In another embodiment, when the jaw members are in the second approximated position, a knife blade is translated distally to extend through knife channel(s) defined within the jaw members to cut tissue disposed between the jaw members.

BRIEF DESCRIPTION OF THE DRAWINGS

Various embodiments of the presently disclosed forceps are described herein with reference to the drawings, wherein.

DETAILED DESCRIPTION

Figure 1:
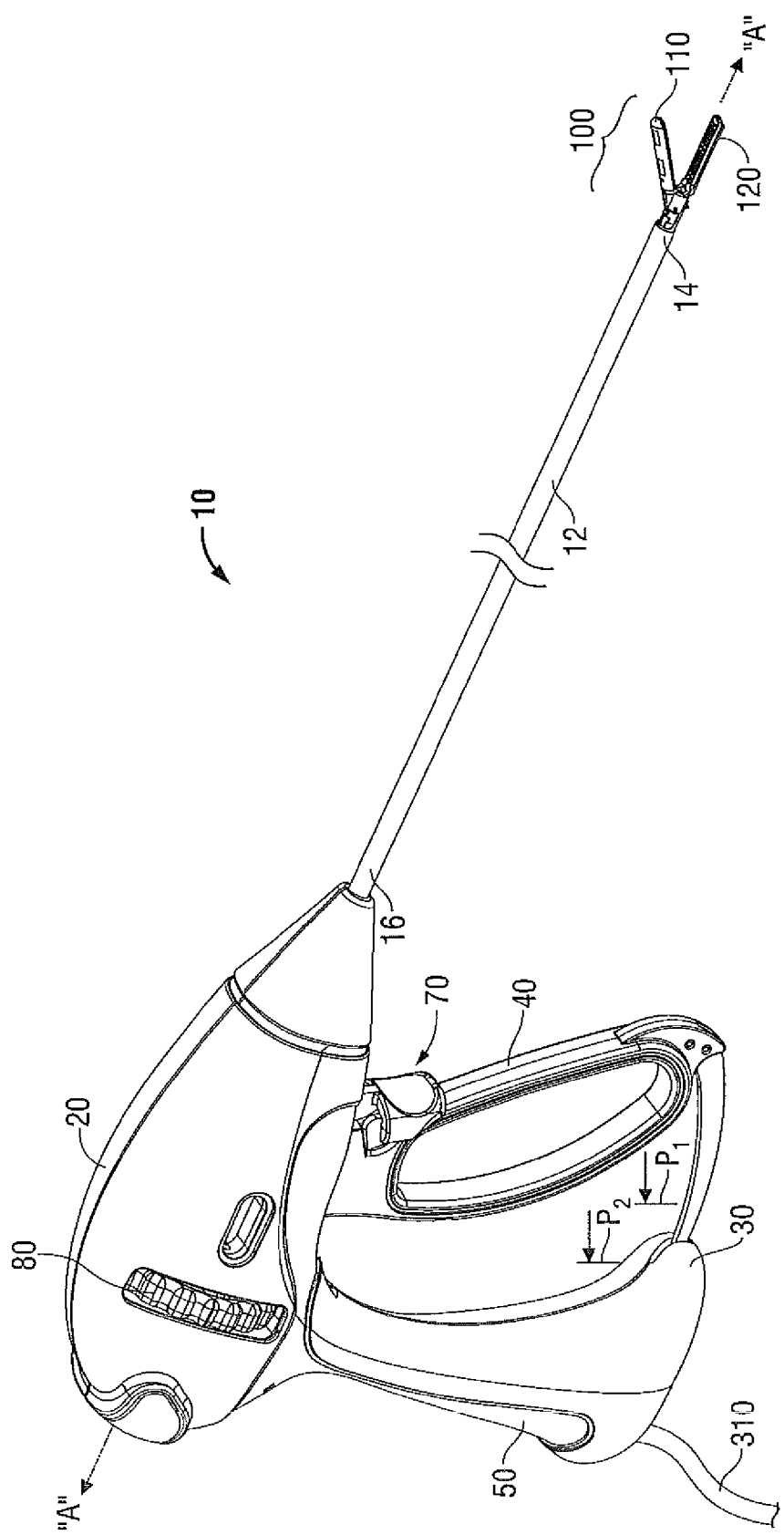
FIG. 1 is a perspective view of a forceps having an end effector assembly in accordance with an embodiment of the present disclosure.

Embodiments of the presently disclosed surgical instrument are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Turning now to FIG. 1, a forceps 10 is provided including a housing 20, a handle assembly 30, an end effector rotating assembly 80, a trigger assembly 70 and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 310 that connects forceps 10 to a generator (not shown) or other suitable power source. Cable 310 has sufficient length to extend through shaft 12 in order to provide electrical energy to at least one of jaw members 110 and 120 of end effector assembly 100. Although shown as an endoscopic surgical instrument, forceps 10 may also be configured as an open, hemostat-style surgical instrument.

With continued reference to FIG. 1, handle assembly 30 includes fixed handle 50 and a moveable handle 40. Fixed handle 50 is integrally associated with housing 20 and handle 40 is moveable relative to fixed handle 50. End effector rotating assembly 80 is rotatable in either direction about a longitudinal axis "A-A" to rotate end effector 100 about longitudinal axis "A-A." The housing 20 houses the internal working components of the forceps 10.

Figure 2:
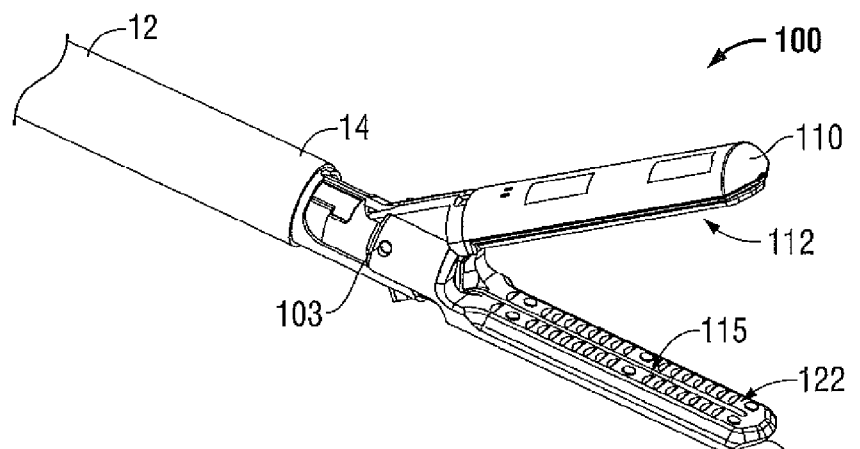
FIG. 2 is an enlarged, perspective view of the end effector assembly of the forceps of FIG. 1.

Turning now to FIG. 2, end effector assembly 100 is shown attached at a distal end 14 of shaft 12 and includes a pair of opposing jaw members 110 and 120. Each of jaw members 110 and 120 includes an electrically conductive tissue sealing surface 112 and 122, respectively, that is dimensioned to oppose the other as shown in FIG. 2. End effector assembly 100 is designed as a unilateral assembly, i.e., jaw member 120 is fixed relative to the shaft 12 and jaw member 110 is moveable about a pivot 103 relative to jaw member 120. However, either, or both jaw members 110, 120 may be moveable with respect to the other. In some embodiments, as will be described in greater detail hereinbelow, a knife assembly 140 (FIG. 9) is disposed within shaft 12 and a knife channel 115 is defined within one or both jaw members 110, 120 to permit reciprocation of a knife blade 146 (FIGS. 9 and 10) therethrough.

Referring back to FIG. 1, moveable handle 40 of handle assembly 30 is ultimately connected to a drive assembly (not shown) that, together, mechanically cooperate to impart movement of jaw members 110 and 120 between an open position, a first approximated position, and a second approximated position to grasp, seal, and divide, tissue disposed between sealing surfaces 112 and 122 (FIG. 2). As shown in FIG. 1, moveable handle 40 is initially spaced-apart from fixed handle 50 and, correspondingly, jaw members 110, 120 are in the open, or spaced-apart position. Moveable handle 40 is depressible from the initial position to an intermediate position "$P_1$", corresponding to the first approximated position of jaw members 110, 120, and, further, to a depressed position "$P_2$", corresponding to the second approximated position of jaw members 110, 120.

When moveable handle 40 is moved to the intermediate position "$P_1$", e.g., when jaw members 110, 120 are moved to the first approximated position, a specific sealing pressure is applied to tissue disposed therebetween. When moveable handle 40 is moved to the depressed position "$P_2$", e.g., when jaw members 110, 120 are moved to the second approximated position, a specific cutting pressure is applied to tissue disposed therebetween. Accordingly, handle assembly 30 may be configured as a two-step mechanism, e.g., moveable handle 40 may be configured to first move to the intermediate position "$P_1$" and then, upon the application of additional force, move from the intermediate position "$P_1$" to the depressed position "$P_2$", or, alternatively, may be configured as a continuous, single stroke mechanism, e.g., moveable handle 40 is moved from the initial position through the intermediate position "P₁" for sealing tissue and to the depressed position "P₂" for cutting tissue. Other configurations of handle assembly 30 are also contemplated, so long as handle assembly 30 is configured to move jaw member 110, 120 at least between the open position, the first approximated position, and the second approximated position.

Various embodiments of end effector assemblies configured for use with surgical forceps 10 will now be described in detail with reference to FIGS. 3-12. More particularly, each pair of jaw members is configured for movement between a spaced-apart position, a first approximated position, and a second approximated position. When moveable handle 40 is moved to the intermediate position "P₁" (FIG. 1), corresponding to the first approximated position, a sealing pressure is applied to tissue disposed between the jaw members. Electrosurgical energy may be communicated to the electrically conductive sealing surfaces of the respective jaw members, e.g., by actuation of trigger 70 (FIG. 1), to seal tissue disposed therebetween when the jaw members are disposed in the first approximated position. When moveable handle 40 is moved to the depressed position "P₂" (FIG. 1), corresponding to the second approximated position, a cutting pressure is applied to tissue disposed between the jaw members. Each pair of jaw members according to the various embodiments described below is configured to perforate, partially cut, and/or completely divide tissue disposed between the jaw members when the jaw members are moved to the second approximated position. As mentioned above, in some embodiments, e.g., where tissue is not fully divided, a knife blade 146 (FIG. 9) may be advanced through the jaw members to divide the perforated or partially cut tissue.

Figure 3:
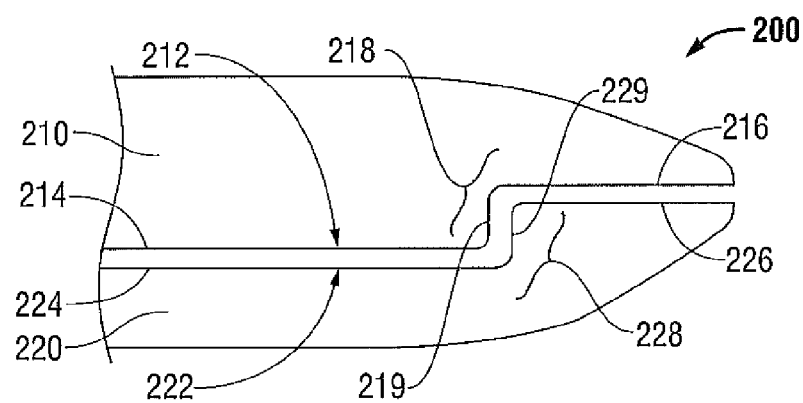
FIG. 3 is a side, cross-sectional view of one embodiment of jaw members for use with the end effector assembly of FIG. 1.

Referring now to FIG. 3, an end effector assembly 200 configured for use with surgical forceps 10 includes first and second jaw members 210 and 220, respectively, disposed in opposing relation relative to one another and including opposed electrically conductive sealing surfaces 212, 222, respectively. Sealing surfaces 212, 222 of jaw members 210, 220, respectively, define complementary "stepped" cross-sectional profiles, as shown in FIG. 3. More specifically, each sealing surface 212, 222 includes a proximal portion 214, 224 and a distal portion 216, 226 interconnected by a "stepped" portion 218, 228, respectively, defined longitudinally therealong. The stepped portions 218, 228 include steps 219, 229, respectively, that offset the proximal portions 214, 224 and distal portions 216, 226 of the respective sealing surfaces 212, 222 from one another. Thus, as shown in FIG. 3, proximal portion 214 of sealing surface 212 of jaw member 210 is offset below distal portion 216 of sealing surface 212 of jaw member 210 and, similarly, proximal portion 224 of sealing surface 222 of jaw member 220 is offset below distal portion 226 of sealing surface 222 of jaw member 220.

The complementary stepped portions 218, 228 of sealing surfaces 212, 222 of jaw members 210, 220, respectively, may be positioned more proximally or more distally along the respective jaw members 210, 220 than as shown in FIG. 3. Alternatively, the complementary stepped portions 218, 228 may be defined laterally across sealing surfaces 212, 222 of jaw members 210, 220 to define a "stepped" front cross-section (see FIG. 11, for example). Further, steps 219, 229 may be angled distally or proximally with respect to sealing surfaces 212, 222 from the substantially perpendicular position shown in FIG. 3. Multiple stepped portions and/or multiple steps positioned along sealing surfaces 212, 222 are also contemplated.

In use, as mentioned above, moveable handle 40 is moved from the initial position to the intermediate position "P₁" (FIG. 1) and, accordingly, jaw members 210, 220 are moved from the spaced-apart position to the first approximated position. In the first approximated position, sealing surfaces 212, 222 grasp tissue disposed therebetween according to a specific sealing pressure. Electrosurgical energy is conducted through sealing surfaces 212, 222 and through tissue to effect a tissue seal.

Upon further depression of moveable handle 40, moveable handle 40 reaches the depressed position "P₂" (FIG. 1) wherein jaw members 210, 220 are moved to the second approximated position to apply a specific cutting pressure to the sealed tissue disposed between sealing surfaces 212, 222 of jaw members 210, 220, respectively. In the second approximated position, the pressure applied by jaw members 210, 220 to tissue, e.g., the cutting pressure, is sufficiently great at stepped portions 218, 228, such that the combination of the tension on tissue and the approximation of steps 219, 229 of complementary stepped portions 218, 228 of sealing surfaces 212, 222, respectively, severs, or divides tissue disposed therebetween.

Figure 4:
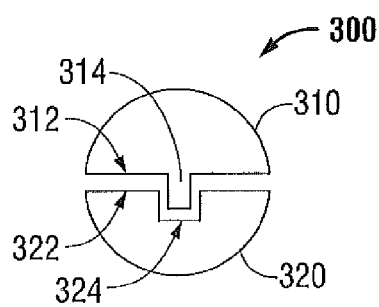
FIG. 4 is a front, cross-sectional view of another embodiment of jaw members for use with the end effector assembly of FIG. 1.

With reference now to FIG. 4, end effector assembly 300 is shown configured for use with surgical forceps 10. End effector assembly 300 includes a pair of jaw members 310, 320, each including an opposed electrically conductive sealing surface 312, 322. Jaw member 310 includes a protrusion, e.g., an elongated flange 314, extending longitudinally along and protruding from sealing surface 312. Elongated flange 314 may define a rectangular front cross-section, as shown in FIG. 4, or may define another cross-section, e.g., circular, square, diamond, etc. Jaw member 320 includes an elongated recess 324 defined within and extending longitudinally along sealing surface 322. Elongated recess 324 is shaped complementary to elongated flange 314, i.e., recess 324 defines a rectangular front cross-section, and may define a substantially equal or slightly larger diameter than elongated flange 314 such that, upon movement of jaw members 310, 320 to the approximated positions, elongated flange 314 is at least partially disposed within elongated recess 324.

In use, moveable handle 40 is moved to the intermediate position "P₁" (FIG. 1) to thereby move jaw members 310, 320 to the first approximated position wherein sealing surfaces 312, 322 impart a specific sealing pressure to tissue grasped therebetween. Electrosurgical energy may then be conducted through sealing surfaces 312, 322 and through tissue to effect a tissue seal.

As in the previous embodiment, depressing moveable handle 40 to the depressed position "P₂" (FIG. 1) moves jaw members 310, 320 to the second approximated position such that a specific cutting pressure is applied to the sealed tissue disposed between sealing surfaces 312 and 322. In the second approximated position, the cutting pressure applied by jaw members 310, 320 to tissue is sufficiently great such that, the tension on tissue and the engagement of protrusion 314 within recessed portion 324, severs, or divides tissue disposed therebetween.

Figure 5:
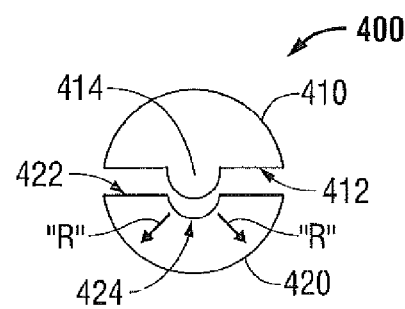
FIG. 5 is a front, cross-sectional view of yet another embodiment of jaw members for use with the end effector assembly of FIG. 1.

Referring now to FIG. 5, end effector assembly 400 is configured for use with surgical forceps 10 and includes a pair of jaw members 410, 420, each including an opposed electrically conductive sealing surface 412, 422. Jaw member 410 includes an elongated half-cylindrical flange 414 extending longitudinally along and protruding from sealing surface 412. Jaw member 420 includes an elongated half-cylindrical cut-out, or recess 424 defined within and extending longitudinally along sealing surface 422. Recess 424 is shaped substantially complementary to flange 414 and may define a substantially equal, or slightly smaller radius as compared to flange 414 such that, upon movement of jaw members 410, 420 to the second approximated position, flange 414 engages recess 424 and, optionally, urges recess 424 to expand in the direction of arrows "R."

In use, end effector assembly 400 operates similarly to end effector assembly 300 in that moveable handle 40 is moved to the intermediate position "$P_1$" (FIG. 1) to impart a specific sealing pressure to tissue such that electrosurgical energy may then be applied to seal tissue disposed between jaw member 410 and 420. As in the previous embodiment, moveable handle 40 is then moved to the depressed position "$P_2$" (FIG. 1) to move jaw members 410, 420 to the second approximated position, thereby applying a specific cutting pressure to the sealed tissue disposed between sealing surfaces 412 and 422 and, more particularly, to tissue disposed between cylindrical portion 414 and cylindrical recess 424. In the second approximated position, cylindrical protrusion 414 of jaw member 410 engages cylindrical recess 424 of jaw member 420 and urges cylindrical recess 424 to expand in the direction of arrows "R." The tension on tissue disposed between cylindrical protrusion 414 and cylindrical recess 424 and the engagement of protrusion 414 within recess 424 when jaw member 410, 420 are in the second approximated position causes tissue disposed therebetween to be cut, or divided.

Figure 6A:
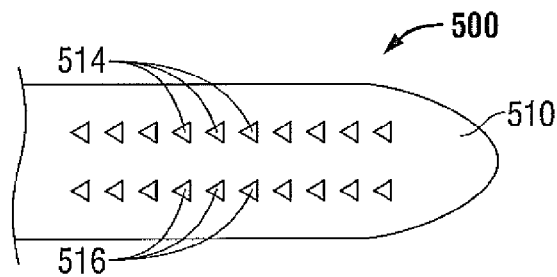
FIG. 6A is a top view of a still another embodiment of a jaw member for use with the end effector assembly of FIG. 1.
Figure 6B:
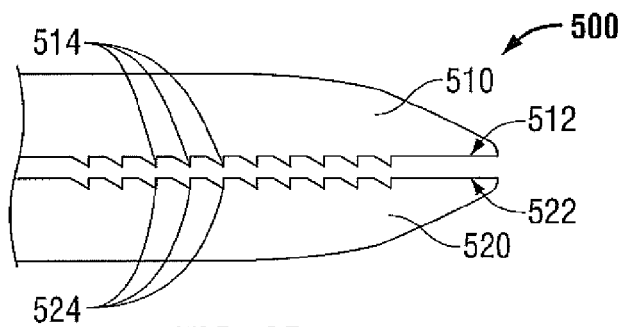
FIG. 6B is a side, cross-sectional view of the jaw member of FIG. 6A and a corresponding jaw member for use with the end effector assembly of FIG. 1.

Turning now to FIGS. 6A-6B, end effector assembly 500 is configured for use with surgical forceps 10 and includes first and second jaw members 510 and 520, respectively. Jaw member 510, as shown in FIG. 6A, includes a plurality of protrusions 514, 516 extending therefrom. More specifically, protrusions 514 form a first column extending longitudinally along sealing surface 512 and protrusions 516 form a second column extending longitudinally along sealing surface 512. The configuration of protrusions 514, 516 shown in FIG. 6A is an example of one configuration; however, protrusions 514, 516 may define greater or fewer columns, or may be arranged in different configurations. Further, the protrusions 514, 516 need not be triangular, as shown in FIGS. 6A-6B, but may, for example, define a square, diamond, or other shape configuration.

As shown in FIG. 6B, jaw member 520 includes a column of triangular recesses, or detents 524 defined within sealing surface 522 and extending longitudinally therealong. Triangular detents 524 are shaped and positioned complementarily to protrusions 514. A second column of detents (not shown) complements column of protrusions 516 such that, as jaw members 510, 520 are moved to the approximated positions, protrusions 514, 516 engage complementary shaped detents 524, (not shown). As with protrusions 514, 516, detents 524 need not be arranged in the configuration shown in FIG. 6A, so long as detents 524 are positioned and configured complementarily to protrusions 514, 516. Further, the configuration of protrusions 514, 516 and detents 524 may be reversed, e.g., protrusions 514, 516 may be positioned along sealing surface 522 of jaw member 520 and detents 524 may be defined within sealing surface 512 of jaw member 510, or jaw members 510 and 520 may include complementary sealing surfaces 512, 522, respectively, including complementary protrusions 514, 516 and detents 524 on each of jaw members 510, 520.

In use, as in the previous embodiments, moveable handle 40 is moved to the intermediate position "$P_1$" (FIG. 1) for sealing tissue. In the intermediate position "$P_1$" (FIG. 1) a specific sealing pressure is imparted to tissue grasped between jaw member 510, 520 and electrosurgical energy is conducted through sealing surfaces 512, 522 and through tissue to effect a tissue seal.

Jaw members 510, 520 are then moved to the second approximated position by depressing moveable handle 40 to the depressed position "$P_2$" (FIG. 1). In this position, a specific cutting pressure is applied to the sealed tissue disposed between sealing surfaces 512 and 522. With the application of the cutting pressure to tissue disposed between jaw members 510, 520, the engagement of protrusions 514, 516 within complementary recesses 524, (not shown) acts to perforate tissue disposed between protrusions 514, 516 and recesses 524, (not shown). With columns of perforations in tissue, tissue may more easily be torn, or divided. Additionally, a knife channel (not shown) may be defined within one (or both) sealing surfaces 512, 522 such that, a knife blade, e.g., knife blade 146 (FIG. 9) of knife assembly 140 (FIG. 9), may be advanced through the perforated tissue to more easily sever tissue. In such an embodiment, the incidents of blade splay would be reduced since blade 146 (FIG. 9) would more easily cut through the perforated (weakened) tissue as blade 146 (FIG. 9) is advanced distally through the knife channel 115 (FIG. 2).

Figure 7A:
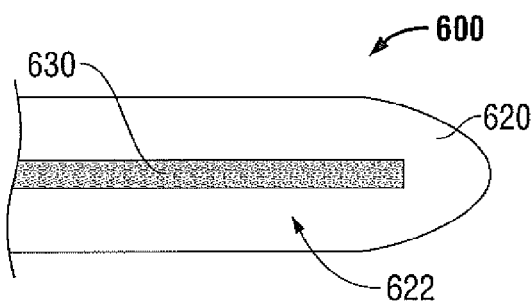
FIG. 7A is a top view of still yet another embodiment of a jaw member for use with the end effector assembly of FIG. 1.
Figure 7B:
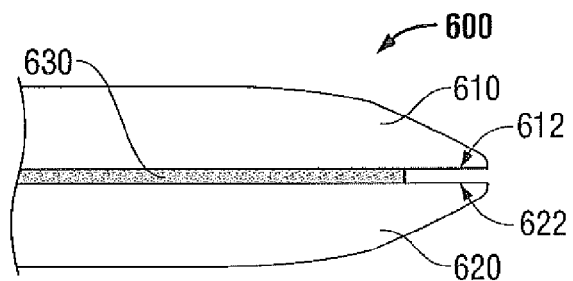
FIG. 7B is a side, cross-sectional view of the jaw member of FIG. 7A and a corresponding jaw member for use with the end effector assembly of FIG. 1.
Figure 7C:
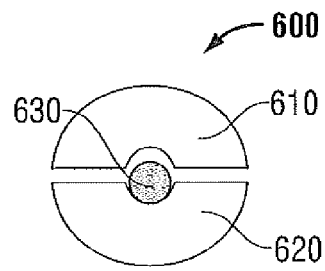
FIG. 7C is a front, cross-sectional view of another embodiment of the jaw end effector assembly of FIG. 7A.

With reference now to FIGS. 7A-7B, an end effector assembly 600 configured for use with surgical forceps 10 includes first and second jaw members 610, 620, respectively. Each jaw member includes an opposed sealing surface 612, 622, respectively. One, or both jaw members, e.g., jaw member 620 (FIG. 7A), may include a ceramic bar 630 extending longitudinally therealong. Ceramic bar 630 may be centered with respect to jaw member 620 (as shown) or may be positioned off-center. Upon movement of jaw members 610, 620 to the approximated positions, as shown in FIG. 7B, ceramic bar 630 of jaw member 620 approaches a mating relationship with sealing surface 612 (or the corresponding ceramic bar) of jaw member 610. Alternatively, as shown in FIG. 7C, ceramic bar 630, which extends along jaw member 620, may define a circular cross-section and may be configured to cooperate with a recess defined within jaw member 620 upon movement of jaw members 610, 620 to the approximated positions.

In use, as mentioned above, moveable handle 40 is moved from the initial position to the intermediate position "$P_1$" (FIG. 1) and, accordingly, jaw members 610, 620 are moved to the first approximated position. With the jaw members applying a specific sealing pressure, electrosurgical energy is conducted through sealing surfaces 612, 622 and through tissue to effect a tissue seal. When jaw members 610, 620 are in the first approximated position, ceramic bar 630 may function to define a gap distance between sealing surfaces 612, 622. Moving jaw members 610, 620 to the second approximated position (corresponding to position "$P_2$" (FIG. 1)) applies a specific cutting pressure to tissue disposed between ceramic bar 630 of jaw member 620 and sealing surface 612 of jaw member 610. More particularly, in the second approximated position, ceramic bar 630 is urged through tissue to divide tissue disposed therebetween.

Figure 8A:
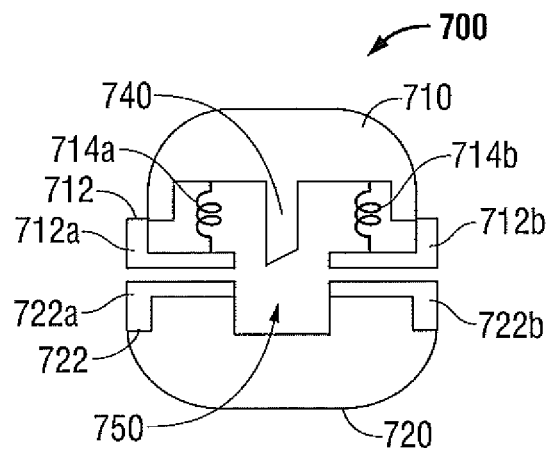
FIG. 8A is a front, cross-sectional view of another embodiment of jaw members for use with the end effector assembly of FIG. 1 showing a sealing surface of one of the jaw members spaced from the jaw member.
Figure 8B:
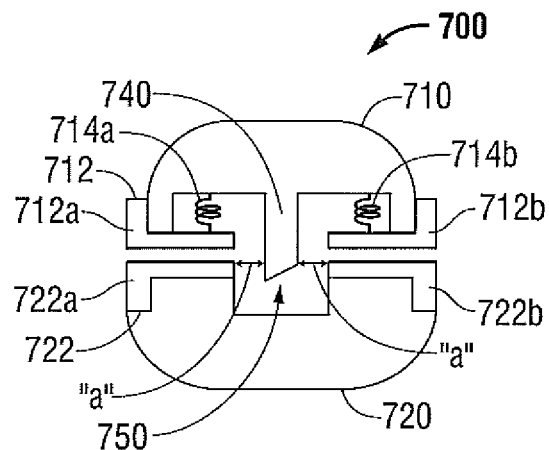
FIG. 8B is a front, cross-sectional view of the jaw members of FIG. 8A showing the sealing surface of one of the jaw members positioned closer to the jaw member.

Turning now to FIGS. 8A-8B, an end effector assembly 700 configured for use with surgical forceps 10 includes first and second jaw members 710 and 720, respectively. Jaw member 710 includes an electrically conductive sealing plate 712, and more particularly, electrically conductive sealing plate halves 712a and 712b that are moveably coupled to jaw member 710 via springs, or actuators 714a, 714b (collectively springs 714). Springs, or actuators 714 may include cantilever beams, coil springs, shape memory materials, hydraulic members, cam members, elastomers, or the like. Springs 714 bias sealing plate 712 toward a spaced-apart position with respect to jaw member 710 and are compressible such that sealing plate 712 is moveable to a closer position with respect to jaw member 710. Jaw member 710 further includes a blade 740 fixedly engaged to jaw member 710 and extending longitudinally at least partially therealong. Initially, as shown in FIG. 8A, when sealing plate 712 is in the spaced-apart position with respect to jaw member 710, blade 740 is disposed within jaw member 710, i.e., blade 740 is not exposed. Upon compression of springs 714 (or retraction of actuators 714), as shown in FIG. 8B, sealing plate halves 712a, 712b are moved to the closer position with respect to jaw member 710 such that blade 740 extends beyond sealing plate 712, i.e., blade 740 is exposed. Springs 714 may be configured to compress upon application of the cutting pressure to tissue disposed between jaw members 710, 720, e.g., upon movement of jaw members 710, 720 to the second approximated position, such that when jaw members are moved to the second approximated position, blade 740 is advanced through tissue disposed between jaw members 710 and 720. Further, sealing plate 712 need not be moveably coupled to jaw member 710 by springs 714, but may be coupled thereto by any suitable spring-like, or actuation mechanism. Additionally, the gap distances "a" between blade sealing plate halves 712a, 712b and blade 740 may be varied to achieve a particular cutting characteristic or characteristics.

Continuing with reference to FIGS. 8A-8B, jaw member 720 includes an electrically conductive sealing plate 722 fixedly engaged thereto and opposed to sealing plate 712. Sealing plate 722 includes first and second sealing plate halves 722a, 722b, respectively. A recess 750 is defined within jaw member 720 between first and second sealing plate halves 722a and 722b, respectively. Recess 750 is configured to permit blade 740 to extend into jaw member 720 upon movement of sealing plate 712 to the closer position with respect to jaw member 710, as shown in FIG. 8B. Alternatively, sealing plate halves 722a, 722b may be moveably coupled to jaw member 720 and may include a fixed blade (not shown) disposed therein. In such an embodiment, sealing plate halves 712a and 712b are fixedly engaged to jaw member 710 on either side of a recess (not shown). In other words, the configuration of jaw members 710 and 720 may be reversed to achieve the same result as described above.

In use, moveable handle 40 is moved from the initial position to the intermediate position "P₁" (FIG. 1) and, accordingly, jaw members 710, 720 are moved from the spaced-apart position to the first approximated position to grasp tissue therebetween. In the first approximated position, sealing plates 712, 722 grasp tissue according to a specific sealing pressure. Springs 714a, 714b are configured with a sufficient stiffness such that, when the sealing pressure is applied, i.e., when jaw members 710, 720 are in the first approximated position, sealing plate 712 remains spaced from jaw member 710, i.e., springs 714 are not compressed. Accordingly, in the first approximated position, fixed blade 740 is not exposed (See FIG. 8A). Electrosurgical energy may be conducted through sealing plates 712, 722 and through tissue to effect a tissue seal when jaw members 710, 720 are in this first approximated position.

Upon further depression of moveable handle 40 to the depressed position "P₂" (FIG. 1), jaw members 710, 720 are moved to the second approximated position wherein a specific cutting pressure is applied to the sealed tissue disposed between sealing plates 712 and 722. The cutting pressure is sufficiently great to compress springs 714a, 714b such that sealing plate 712 is moved to the closer position with respect to jaw member 710. As sealing plate 712 is moved toward jaw member 710, fixed blade 740 is exposed, eventually advancing through tissue disposed between sealing plates 712, 722 and into recess 750, as shown in FIG. 8B. As fixed blade 740 is advanced through tissue, fixed blade 740 cuts, or divides tissue.

Figure 9:
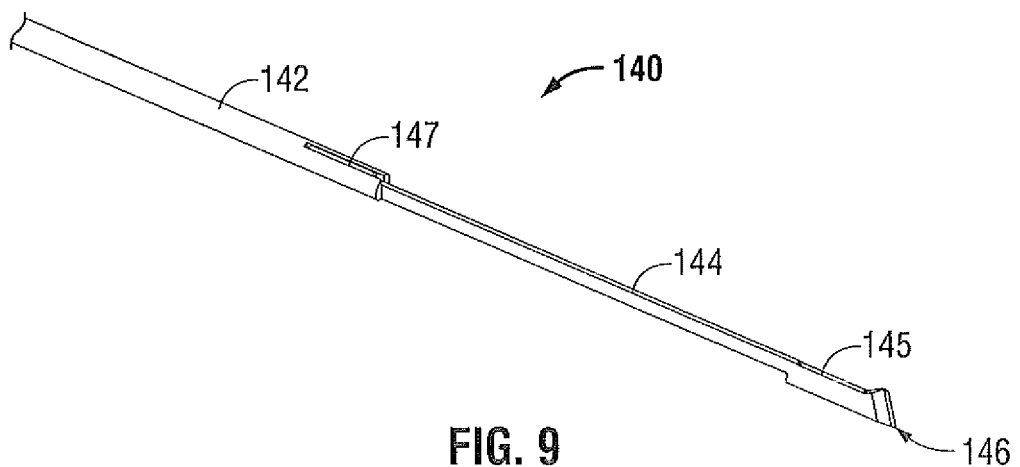
FIG. 9 is a perspective view of a knife assembly in accordance with the present disclosure.
Figure 10:
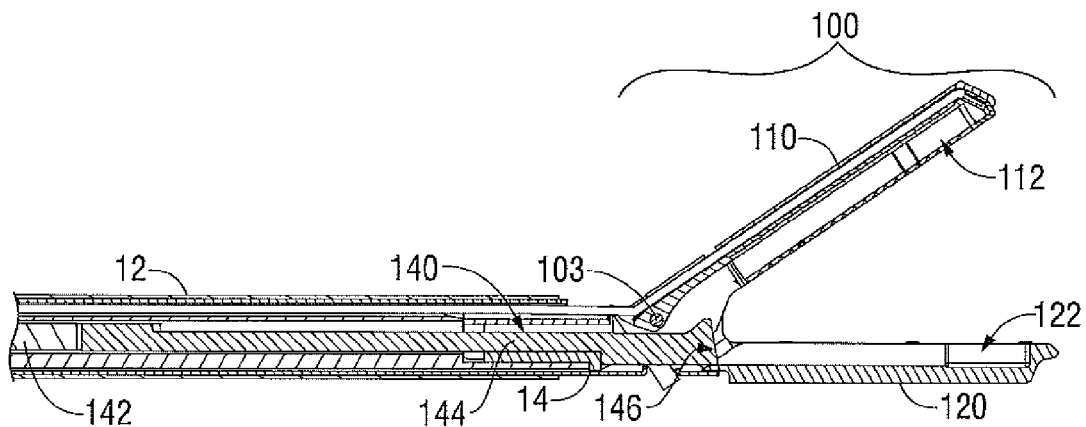
FIG. 10 is a side, cross-sectional view of the end effector assembly of the forceps of FIG. 1.

With reference now to FIGS. 9 and 10, knife assembly 140 is shown including a knife rod 142, a knife bar 144, and a knife blade 146 disposed at a distal end 145 of knife bar 144. A proximal end 147 of knife bar 144 is fixedly engaged to knife rod 142, e.g., via a pin-aperture engagement. Knife assembly 140 is positioned within shaft 12, as best shown in FIG. 10, and is selectively translatable to advance knife blade 146 distally into knife channel(s) 115 (see FIG. 2) defined within either or both jaw members 110, 120 to cut tissue disposed between the jaw members 110, 120. Knife assembly 140, including knife channel 115 may be provided for use with the embodiments described below, or with any of the embodiments above, to facilitate cutting of tissue disposed between jaw members 110, 120 when jaw members 110, 120 are disposed in the second approximated position.

Figure 11:
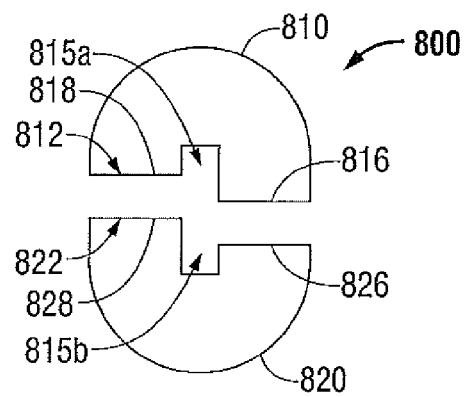
FIG. 11 is a front, cross-sectional view of another embodiment of jaw members for use with the end effector assembly of FIG. 1.

Referring now to FIG. 11 in conjunction with FIGS. 9 and 10, end effector assembly 800 is configured for use with surgical forceps 10 and includes first and second jaw members 810, 820 each having an opposed electrically conductive sealing surface 812, 822, respectively. More specifically, each jaw member 810, 820 includes a pair of sealing surface portions, or halves 816, 818 and 826, 828, respectively, separated by knife channel halves 815a, 815b, respectively. Upon movement of jaw members 810, 820 to the second approximated position, knife channel halves 815a, 815b align to form a complete knife channel configured to permit reciprocation of a knife blade 146 (FIG. 10) therethrough.

As shown in FIG. 11, sealing surface portions, or halves 816 and 818 are offset from one another and similarly, sealing surface halves 826 and 828 are offset from one another. More particularly, sealing surface halves 816 and 826 are offset above sealing surface halves 818 and 828, respectively, such that each jaw member 810, 820 defines a complementary "stepped" front cross-section, with knife channels 815a, 815b, respectively, therebetween.

In use, when jaw members 810, 820 are moved to the first approximated position, sealing surfaces 812, 822 grasp tissue disposed therebetween according to a specific sealing pressure. More particularly, sealing surface halves 816 and 826 grasp tissue on one side of knife channels 815a, 815b and sealing surface halves 818 and 828 grasp tissue on the other side of knife channels 815a, 815b. Electrosurgical energy is conducted through the sealing surfaces 812, 822 and through tissue to effect a tissue seal on both sides of knife channels 815a, 815b.

Moveable handle 40 is then moved to the depressed position "P₂" (FIG. 1) to move jaw members 810, 820 to the second approximated position. In the second approximated position, the pressure, e.g., the cutting pressure, applied to tissue disposed between sealing surface halves 816, 826 and 818, 828 and the offset configuration of jaw members 810, 820 tensions tissue positioned between knife channels 815a, 815b. This tension itself may tear tissue disposed between knife channels 815a and 815b, and/or may provide weakened tissue such that a user may advance knife blade 146 of knife assembly 140 from the shaft 12 and into the knife channels 815a, 815b to more easily sever the weakened tissue.

Figure 12:
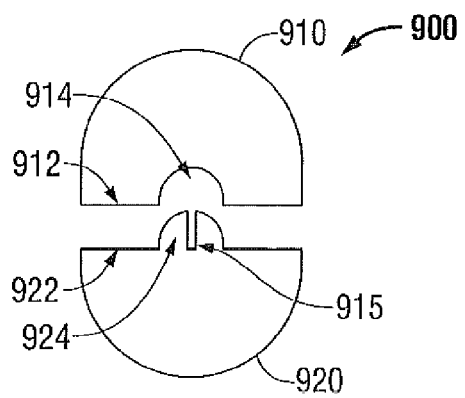
FIG. 12 is a front, cross-sectional view of still another embodiment of jaw members for use with the end effector assembly of FIG. 1.

Turning now to FIG. 12 in conjunction with FIGS. 9 and 10, end effector assembly 900 is configured for use with surgical forceps 10 and includes first and second jaw members 910 and 920. Jaw member 910 includes an electrically conductive sealing surface 912 that opposes an electrically conductive sealing surface 922 disposed on jaw member 920. Jaw member 910 further includes a cylindrical-shaped recess 914 defined therein and extending therealong. Jaw member 920 includes a complementary cylindrical-shaped portion 924 protruding therefrom and extending therealong. A knife channel 915 is defined within cylindrical-shaped protrusion 924 such that, upon movement of jaw members 910, 920 to the second approximated position, knife blade 146 (FIG. 10) may be advanced through knife channel 915 to cut tissue disposed between jaw members 910 and 920. As in any of the previous embodiments, the configuration of the jaw members 910, 920 may be reversed.

In use, end effector assembly 900 operates similarly to end effector assembly 800. Thus, jaw members 910, 920 are initially moved to the first approximated position for sealing tissue disposed between sealing surfaces 912, 922. Next, jaw members 910, 920 are moved to the second approximated position wherein the cutting pressure and the complementary cylindrical-shaped sections 914, 924 tension tissue disposed between cylindrical-shaped protrusion 924 and cylindrical-shaped recess 914. As in the previous embodiment, this tensioning itself may tear tissue therebetween and/or may provide weakened tissue such that a user may advance knife blade 146 of knife assembly 140 from shaft 12 and into the knife channel 915 to more easily sever the weakened tissue.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A forceps, comprising:
    an end effector assembly including:
        a pair of jaw members disposed in opposing relation relative to one another, at least one jaw member moveable relative to the other between a spaced-apart position, a first approximated position, and a second approximated position, an opposing surface of each jaw member defining a complementary stepped portion, the complementary stepped portions of the respective jaw members defined along the jaw members such that a distal end of each jaw member is offset from a proximal end of each jaw member, the jaw members configured to apply a pre-determined pressure to tissue disposed therebetween in each of the first and second approximated positions, wherein a sealing pressure is applied to tissue disposed between the jaw members when the jaw members are in the first approximated position and wherein a cutting pressure is applied to tissue disposed between the jaw members when the jaw members are in the second approximated position such that tissue disposed between the jaw members is cut by the engagement of the complementary stepped portions.

2. The forceps according to claim 1, wherein at least one of the jaw members is adapted to connect to an electrosurgical energy source to communicate energy to tissue disposed between the jaw members to seal tissue disposed therebetween when the jaw members are in the first approximated position.

3. A method of sealing and dividing tissue comprising the steps of:
    providing a forceps including an end effector assembly including a pair of jaw members disposed in opposing relation relative to one another, at least one jaw member moveable relative to the other between a spaced-apart position, a first approximated position, and a second approximated position, an opposing surface of each jaw member defining a complementary stepped portion, the complementary stepped portions of the respective jaw members defined along the jaw members such that a distal end of each jaw member is offset from a proximal end of each jaw member;
    positioning the forceps such that tissue is disposed between the jaw members with the jaw members disposed in the spaced-apart position;
    moving the jaw members from the spaced apart position to the first approximated position to apply a sealing pressure to tissue disposed therebetween;
    sealing tissue disposed between the jaw members; and
    moving the jaw members to the second approximated position to apply a cutting pressure to tissue disposed between the jaw members such that tissue disposed between the jaw members is cut by the engagement of the complementary stepped portions.

4. The method according to claim 3, wherein the sealing step comprises applying electrosurgical energy to the jaw members to seal tissue disposed therebetween when the jaw members are in the first approximated position.

* * * * *